United States Patent
Harrison

(10) Patent No.: US 8,985,114 B2
(45) Date of Patent: Mar. 24, 2015

(54) METHOD AND APPARATUS FOR PORTABLE FLUID DELIVERY FOR ANIMALS

(76) Inventor: Charles Harrison, Sante Fe, NM (US)

(*) Notice: Subject to any disclaimer, the term of this patent is extended or adjusted under 35 U.S.C. 154(b) by 135 days.

(21) Appl. No.: 13/296,057

(22) Filed: Nov. 14, 2011

(65) Prior Publication Data
US 2012/0152242 A1 Jun. 21, 2012

Related U.S. Application Data

(60) Provisional application No. 61/413,100, filed on Nov. 12, 2010.

(51) Int. Cl.
*A61D 7/04* (2006.01)
*A62B 7/00* (2006.01)
*A62B 18/06* (2006.01)
*A61M 16/06* (2006.01)

(52) U.S. Cl.
CPC ........................................ *A61D 7/04* (2013.01)
USPC ............ 128/207.11; 128/205.25; 128/203.12; 128/203.29; 128/205.22

(58) Field of Classification Search
USPC ............. 128/200.24, 203.12, 203.29, 204.18, 128/205.25, 206.12–206.19, 128/206.21–207.12, 207.13, 207.18; 54/80.1–80.5; 119/66, 67, 72, 72.5
See application file for complete search history.

(56) References Cited

U.S. PATENT DOCUMENTS

| | | | | | |
|---|---|---|---|---|---|
| 4,546,768 | A | * | 10/1985 | Ferierabend | 128/200.16 |
| 5,566,645 | A | * | 10/1996 | Cole | 119/712 |
| 5,954,049 | A | * | 9/1999 | Foley et al. | 128/203.29 |
| 6,044,844 | A | | 4/2000 | Kwok | |
| 7,077,126 | B2 | * | 7/2006 | Kummer et al. | 128/200.23 |
| 7,255,107 | B1 | | 8/2007 | Gomez | |
| 2005/0061326 | A1 | * | 3/2005 | Payne, Jr. | 128/206.11 |
| 2005/0279351 | A1 | * | 12/2005 | Lewis et al. | 128/200.23 |
| 2007/0068124 | A1 | * | 3/2007 | Dyck et al. | 54/80.1 |
| 2009/0187161 | A1 | | 7/2009 | Hatch | |
| 2009/0301484 | A1 | | 12/2009 | Dunlop | |
| 2011/0061349 | A1 | * | 3/2011 | Lloyd | 54/71 |

* cited by examiner

*Primary Examiner* — Valerie L Skorupa
(74) *Attorney, Agent, or Firm* — Deborah A. Peacock; Justin R. Jackson; Peacock Myers, P.C.

(57) ABSTRACT

Embodiments of the present invention relate to a method and apparatus for supplying a fluid, including but not limited to oxygen and/or medications to a non-human animal in a configuration that does not require a human to hold a component on the animal.

18 Claims, 21 Drawing Sheets

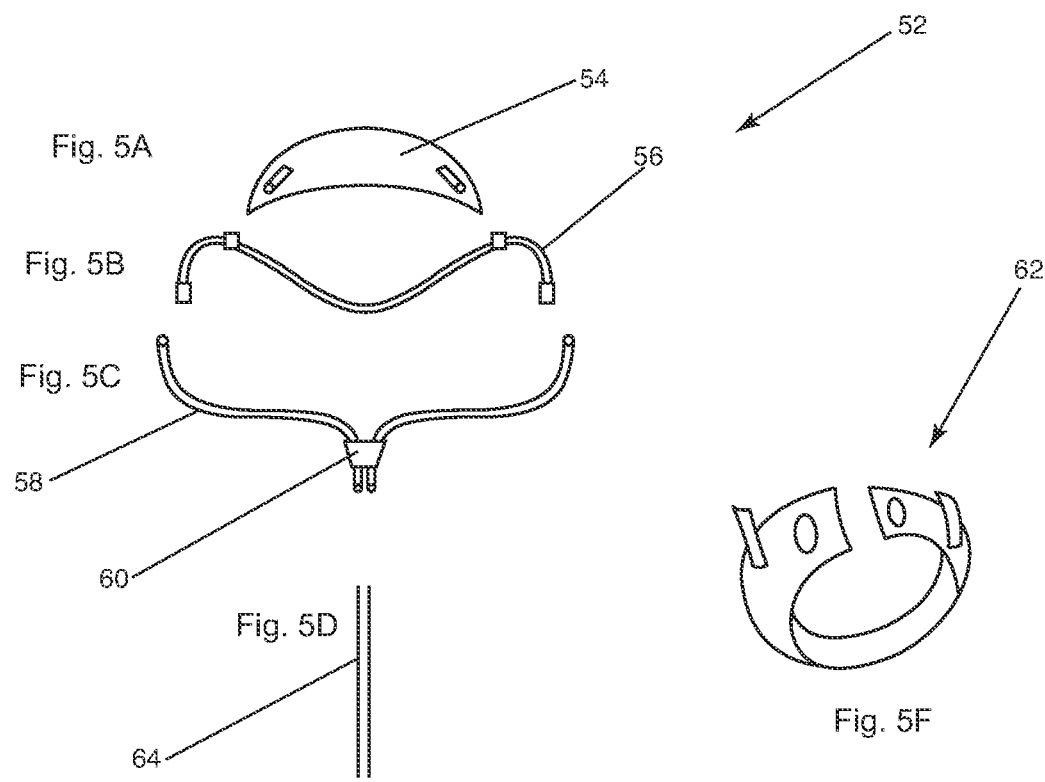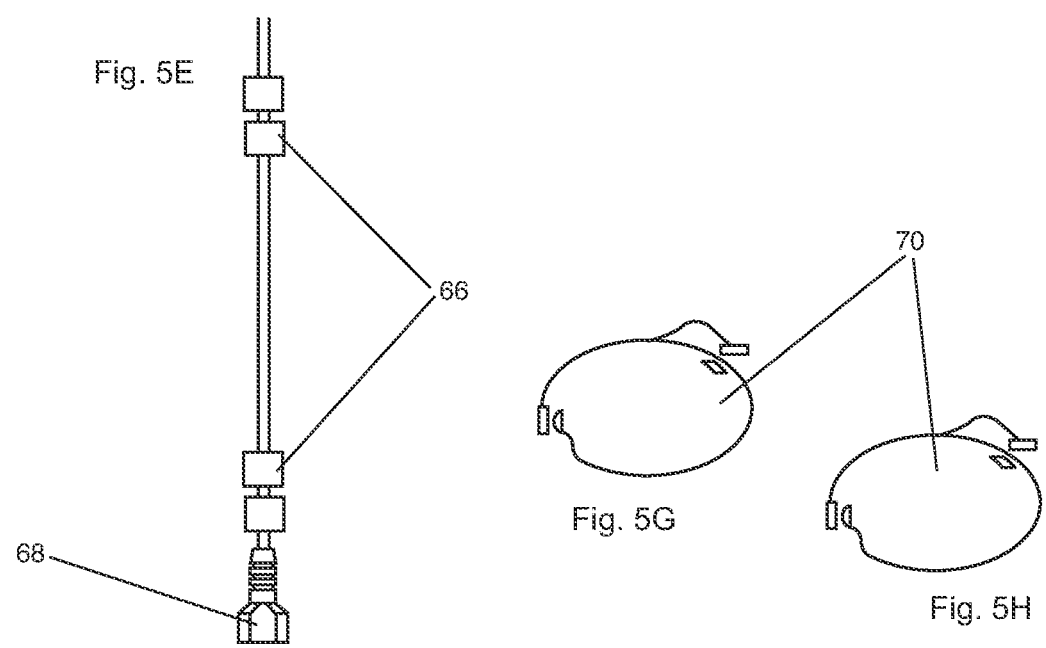

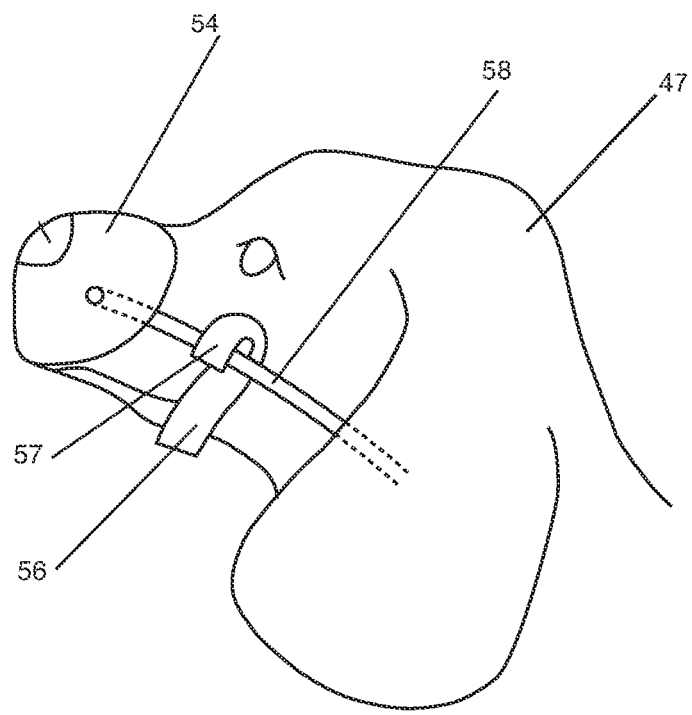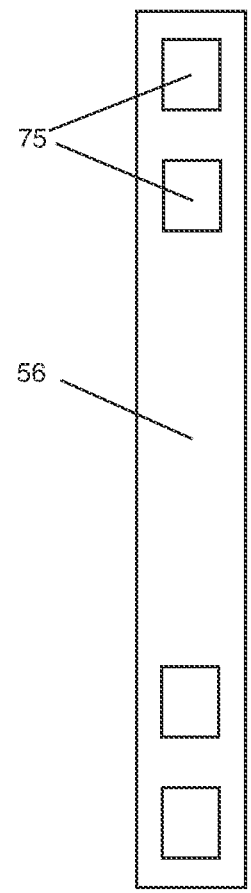
FIG. 8A
FIG. 8B front side top

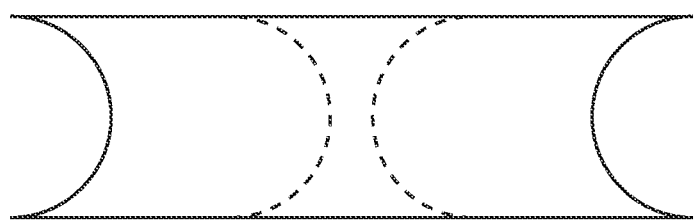
Fig. 15A
top
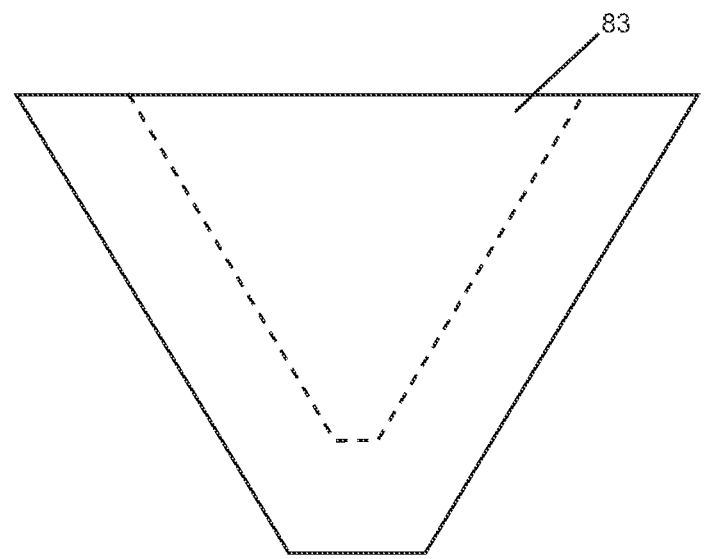
Fig. 15B
front
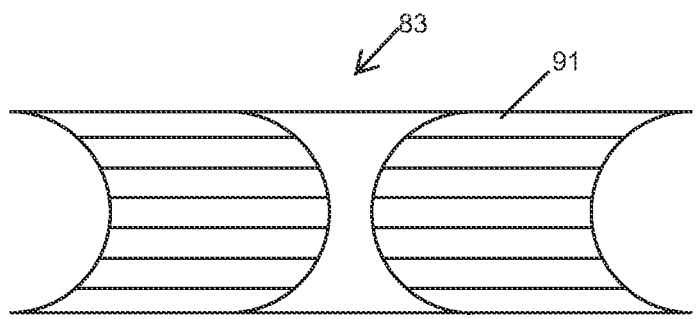
Fig. 15C
bottom
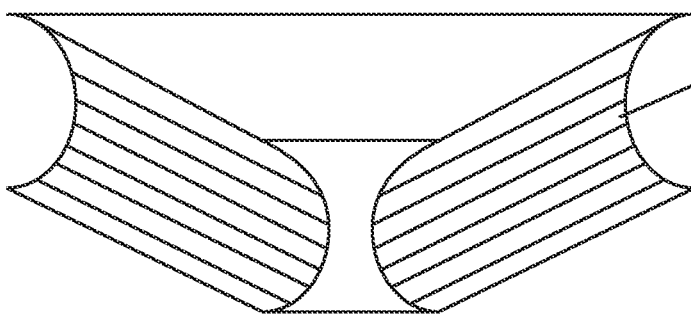
Fig. 15D
perspective

METHOD AND APPARATUS FOR PORTABLE FLUID DELIVERY FOR ANIMALS

CROSS-REFERENCE TO RELATED APPLICATIONS

This application claims priority to and the benefit of the filing of U.S. Provisional Patent Application Ser. No. 61/413,100, entitled "METHOD AND APPARATUS FOR PORTABLE OXYGEN FOR ANIMALS", filed on Nov. 12, 2010, and the specification and claims thereof are incorporated herein by reference.

BACKGROUND OF THE INVENTION

1. Field of the Invention (Technical Field)

Embodiments of the present invention relate to a method and apparatus for providing portable oxygen delivery to animals. Embodiments of the present invention are alternatively suitable for delivery of other fluids.

2. Background

The following discussion refers to information that is given for more complete background and is not to be construed as an admission that such information is prior art for patentability determination purposes.

There are two products currently available that provide oxygen to animals, but they are not portable oxygen devices. One is Aerodawg® (U.S. Trademark Registration No. 3280408, owned by Trudell Medical International Trudell Partnership Holdings Limited and Packard Medical Supply Centre Ltd.), invented by Dr. Philip Padrid. This device is a breathing chamber that is held over a dog's nose and mouth to supply inhaled aerosol medications. However, it must be held in place for only a few seconds at a time to prevent the delivery of an overdose by an attending human.

Similarly, there is an oxygen mask for dogs made and distributed by Invisible Fence, Inc., through its "Project Breathe." This is also a temporary mask that must be held by a human, and is distributed to fire departments throughout the USA and Canada. It is intended for resuscitation of dogs, cats, ferrets, and other small mammals injured in house fires.

For dogs that become "oxygen dependent," the only methods available, until now, have been closed cages with oxygen pumped in via a sealed port, oxygen catheters which are needle-like tubes inserted deep into a nostril and affixed with stitches in the cheek, and cannulae—tight tubes surrounding the head with two stiff probes sticking into the nostrils. While a few dogs will tolerate a catheter, even fewer will tolerate a cannula, but almost all refuse both vehemently. The only other solution is a zippered vinyl tent, replicating the glass oxygen cages in veterinarian hospitals, but none of these solutions allow a dog to enjoy freedom of movement. The cost of intensive care in a veterinarian hospital, with a closed oxygen cage, can cost many hundreds of dollars per day. This almost guarantees that after a few days, at most, oxygen dependent dogs are euthanized. There is thus a present need for a comfortable, non-intrusive mask which can provide supplementary portable oxygen to a non-human animal.

BRIEF SUMMARY OF THE INVENTION

Embodiments of the present invention relate to apparatuses and methods for providing fluid to a non-human animal comprising: at least one portable fluid source; a delivery system apparatus comprising at least one mask and at least one fluid transport tube; and at least one securing belt for disposing the delivery system on the animal. The delivery system comprises a flexible mask. The securing belt may comprise a head strap, at least one underchin strap and/or a harness. One embodiment of the delivery system is preferably configured to hold the transport tube out of reach of teeth of the animal. The present invention allows an animal to eat, drink, sneeze, scratch, sleep in many positions, walk, run, and twirl while the animal is wearing the apparatus. Embodiments of the present invention wherein the fluid delivered to the animal comprises oxygen and/or a medication.

The mask is disposed at least partially around a nose of the non-human animal. The animal may wear the delivery system without requiring a person to hold the mask.

Further scope of applicability of the present invention will be set forth in part in the detailed description to follow, taken in conjunction with the accompanying drawings, and in part will become apparent to those skilled in the art upon examination of the following, or may be learned by practice of the invention. Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings:

FIGS. 5A-H (hereinafter collectively referred to as FIGS. 5) and 6 are drawings which illustrate alternative embodiments for connection of various components of the present invention;

FIGS. 8A-B, and 9A-B illustrate embodiments of under chin straps and the placement thereof on animals;

FIGS. 15 A-D illustrate several views of a wedge;

DETAILED DESCRIPTION OF THE INVENTION

Embodiments of the present invention relate to a method and apparatus for supplying portable oxygen to animals, particularly non-human animals. Embodiments of the present invention preferably comprise a delivery system apparatus which is preferably attached firmly to a nose, without blocking or irritating the animal's mouth, lips, and nostrils. Embodiments of the present invention also optionally include but are not limited to a soft, comfortable harness to keep the oxygen supply tubes close to the animal's body, out of reach of its teeth, and to prevent kinking of the tubes. Embodiments of the harness preferably allow the animal to eat, drink, sneeze, scratch, run, twirl, sleep in many positions, and generally engage in normal behavior. Alternatively, other embodiments can be used to provide the delivery of other fluids, including but not limited to aerosol medications.

The term "animal" as used throughout the specification and claims, means a non-human animal, including in particular, dogs, cats, and other small animals.

The terms "hose", "tubing," "tubes," "pipe," and "pipes" as used throughout the specification and claims, are used to describe any apparatus, method, conduit, passageway or system capable of, conducting and/or transporting fluids, including but not limited to tubing, piping, conduits, tunnels, hoses, combinations thereof, and the like whether flexible, nonflexible, or semi-flexible.

The terms "strap" or "belt", as used interchangeably throughout the specification and claims, includes but is not limited to any material, apparatus, and/or system capable of securing and/or disposing and/or attaching an article to an animal.

Figure 1:
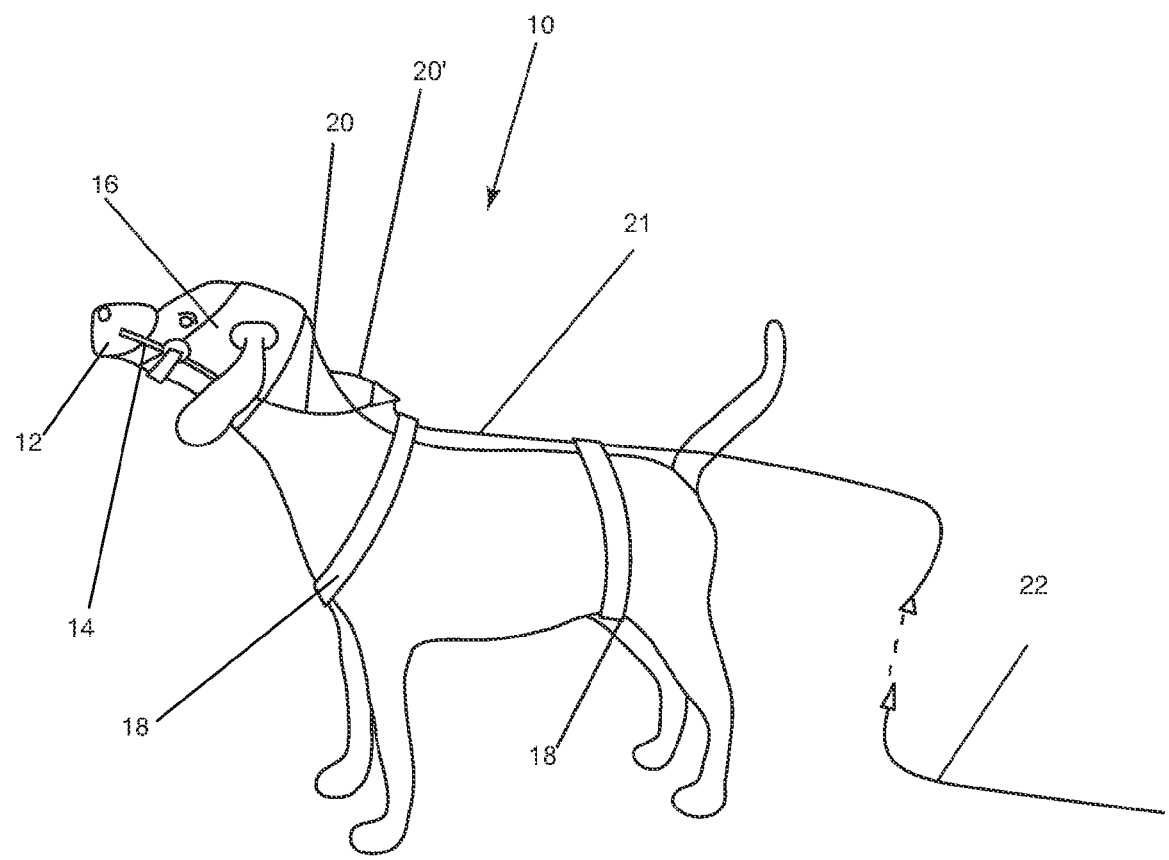
FIG. 1 is a drawing which illustrates an embodiment of the present invention disposed on a dog.

FIG. 1 illustrates an embodiment of the present invention wherein delivery system 10 includes mask 12, inlet tubes 14, head strap 16, belts 18, left and right head tubes 20 and 20', transport tube 21, and supply tube 22. Embodiments of the present invention preferably comprise certified oxygen tubing (e.g., plastic tubing), and/or any similar or otherwise appropriate tubing for delivering a fluid, which fluid is intended to be administered to the animal. Embodiments of the straps of the present invention preferably comprise one or more flexible materials, including but not limited to straps, as well as combinations thereof. Embodiments of the present invention can include, but are not limited to, chocks, tensioners and tighteners to ensure easy re-adjustment of the invention. The straps, belts and harnesses make the apparatus self-supporting, and a human does not have to hold the delivery system and/or any component of the present invention on the animal. Optionally, belts and/or straps can be adjustable to fit substantially any size animal.

Figure 2:
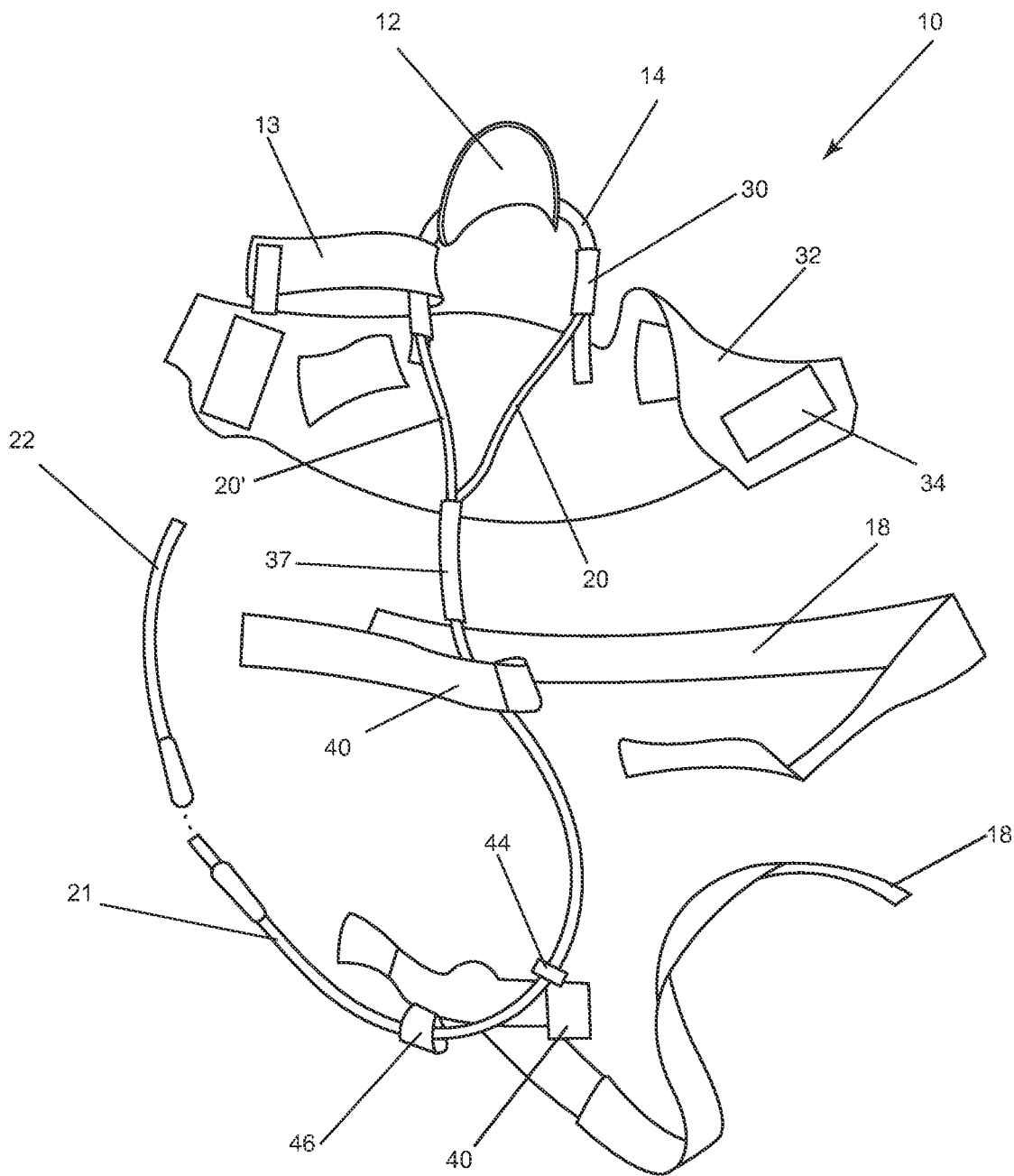
FIG. 2 illustrates the various components of an embodiment of the present invention.

FIG. 2 illustrates an embodiment of the present invention especially useful for dogs and other four-legged animals. As illustrated therein, animal oxygen delivery system 10 comprises mask 12, underchin strap 13, one or more inlet tubes 14, inlet tube connector 30, which is most preferably a tubing connector, left and right head tubes 20 and 20', head strap 32, fastener for head strap 34, first tube ring 37, and belts 18. Tube rings optionally comprise sticky slider rings surrounding a tube until slack is removed. It can act as a "tightener" preferably made of a spiral of rigid ribbon (e.g. plastic). Optionally, belts 18 can comprise a single belt, a plurality of belts, or another structure, including but not limited to a harness, a net, combinations thereof, and the like, which are capable of holding transport tube 21 on an animal, most preferably in an at least semi-fixed position. Optionally, one or more fasteners 40 on at least one of belts 18 holds transport tube 21 in place. This embodiment also preferably comprises second tube ring 44 around transport tube 21. The tube ring can be in used in conjunction with a section of tube that has been made thicker to restrict shifting of transport tube 21 through belt 18. Ring 46 around tube 21 is preferably provided to keep oxygen supply tube 21 connected and to prevent disconnection between supply tube 22 and head tubes 20, 20' and/or inlet tube 14.

Figure 3:
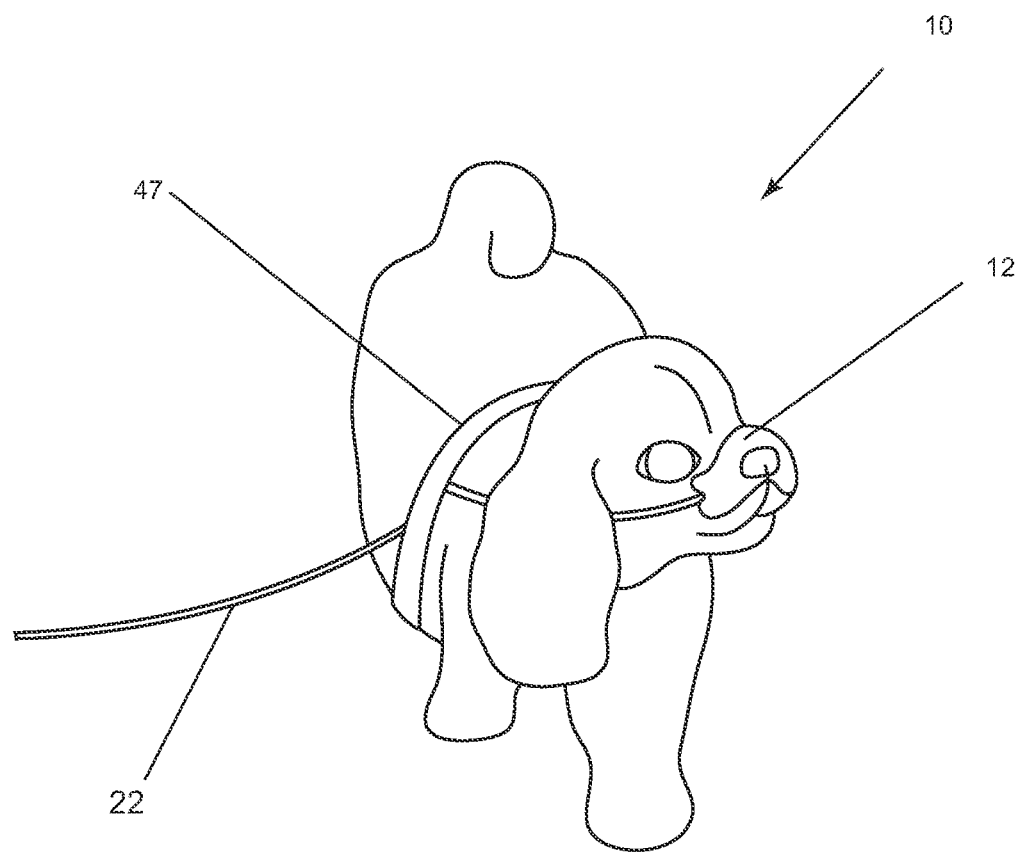
FIGS. 3 and 4 illustrate an embodiment of the present invention attached to a dog.
Figure 4:
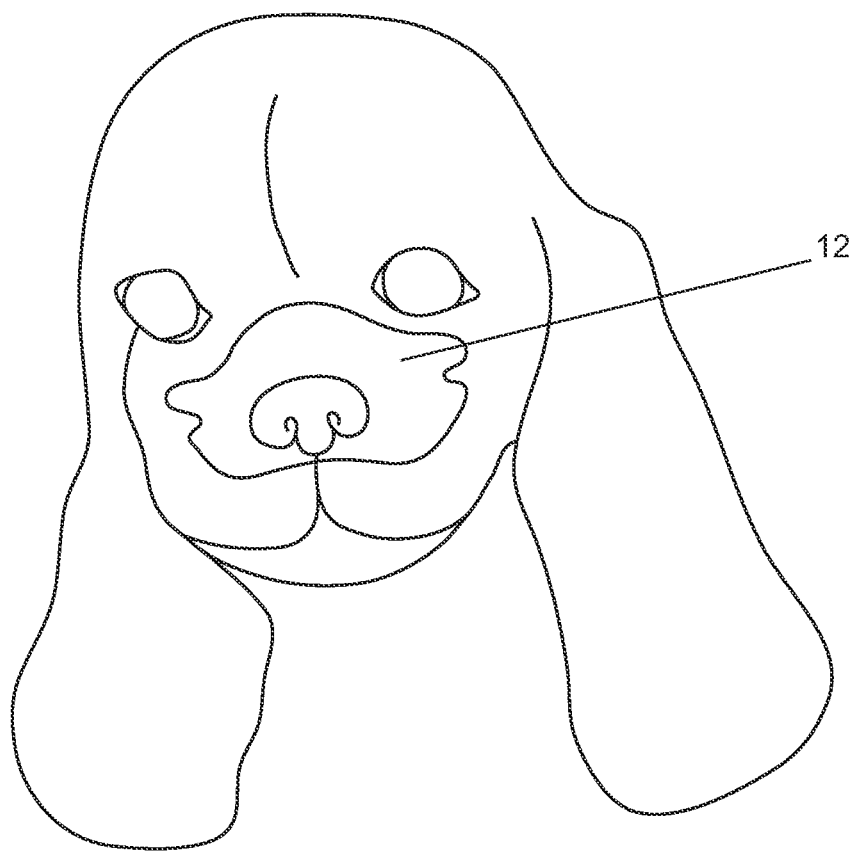

As illustrated in FIGS. 3 and 4 animal oxygen delivery system 10, mask 12 is preferably secure but loose fitting, thus preventing pawing or other methods to remove it by animal 47. Mask 12 preferably fits securely to stay over the nostrils and provide uninterrupted "blow-by" delivery of medication, oxygen, or another fluid, such that it passes by the nostrils of an animal so that the animal can breathe it in. Blow-by is thus distinguished from "injecting", which is accomplished with a cannula. FIG. 3 also identifies fluid supply tube 22.

Alternative embodiments of the present invention comprise a mask that is manufactured in a range of sizes and molded to improve the fit. Metered flow of the fluid delivered by the blow-by action can be increased if some of it is being wasted or diluted too much.

FIGS. 5 through 16 are illustrations of embodiments of the present invention useful for virtually any animal that can benefit from the use of a portable fluid delivery system. FIG. 5 illustrates an embodiment of delivery system 52 comprising a plurality of components, including but not limited to mask 54, underchin strap 56, inlet tubes 58, head strap 62, friction fit chock 60 to keep mask firmly over nose by maintaining tension on tubes 58, transport tube 64, bumpers 66 around tube 64 to prevent tube 64 from sliding forward or backward, connector for transport tubes 68, and belts 70 to hold tubes 64 along the body of an animal. Chock 60 is preferably attached to the inlet tubes 58 by sliding chock onto the tubes and/or attaching in place and then tightening.

Figure 6:
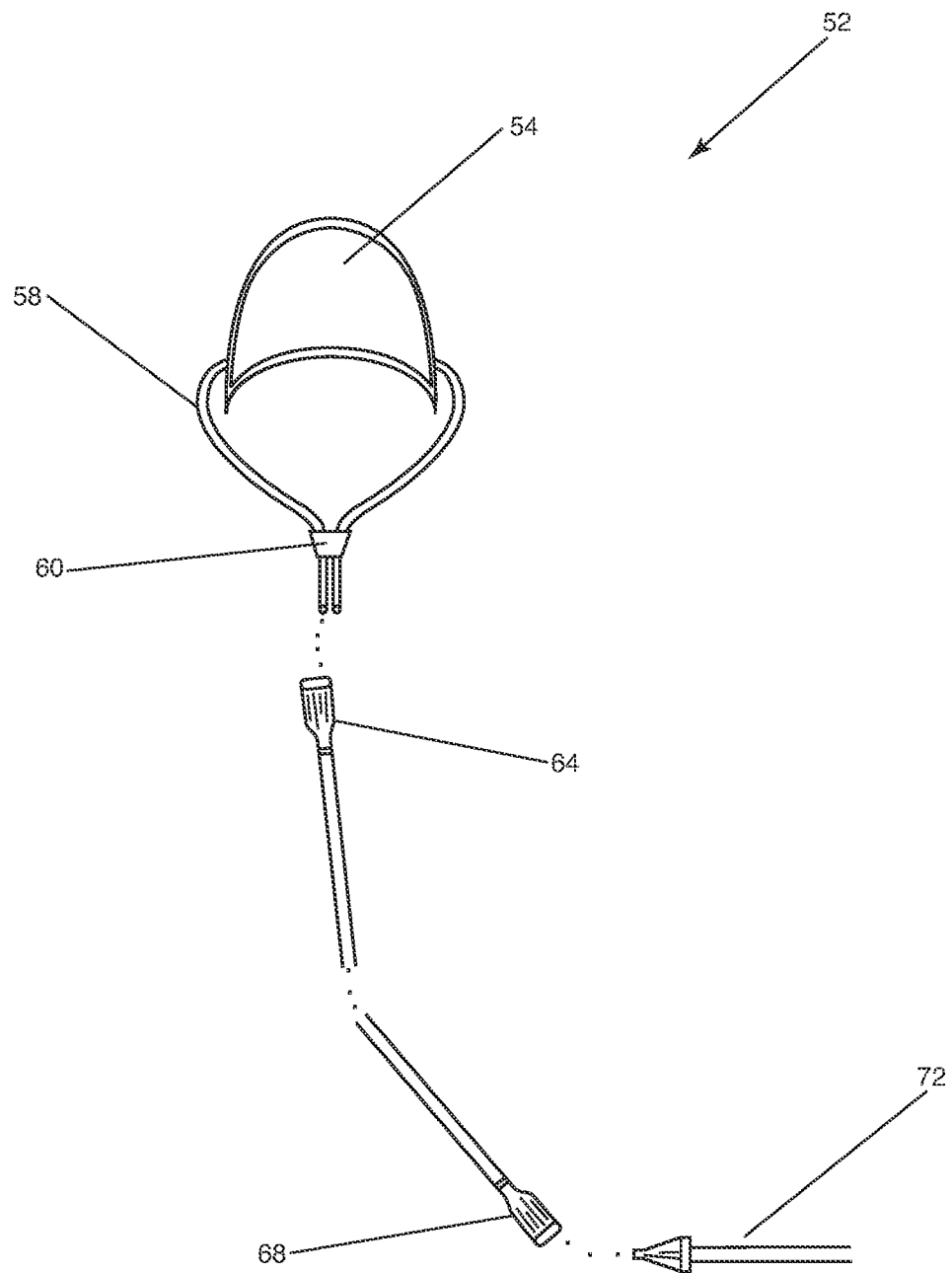

Alternative embodiments of the present invention can be adjustable. One alternative embodiment, as shown in FIG. 6, optionally comprises mask 54 supplied with inlet tubes 58 already attached thereto on one or more sides of the snout of the animal. Optionally, inlet tubes 58 can be threaded loosely through chock 60, bringing them together such that they can be fastened into a junction with transport tube 64. Embodiments of the present invention can be provided in alternative sizes, which have different lengths and/or diameters of inlet tubes 58 between mask 54 and chock 60.

In one embodiment, adjustments to obtain a tight fit around the head of animal 47 can be made with chock 60 after mask 54 is held in place by head strap 62 (see FIG. 5) and chin strap 56. Any tubes that become loose can optionally be adjusted through chock 60.

Chock 60 slides into place and/or can be attached and set in place to achieve a tight fit around the head of animal 47. Bumpers 66 can be slid forward or back along transport tube 64 so that there can be a bumper fore and aft of each body belt 70.

FIG. 6 illustrates inlet tubes 58 which are preferably comprised of light and flexible materials (e.g. polypropylene, polyethylene). Transport tube 64 optionally comprises a larger and more rigid tube than inlet tubes 58. Transport tube 64 can extend the length of the body of an animal and ends at connector 68. At one end, supply tube 72 preferably connects at connector 68 to a supply of fluid (that can include medication) to be delivered at its second end. Optionally, supply tube 72 and can be semi-rigid and/or flexible. Supply tube 72 can comprise a friction fit connection or another type of connection method. Embodiments of the present invention preferably comprise a connection between transport tube 64 and supply tube 72, which is optionally positioned behind a rear belt, but most preferably not positioned so far behind as to be uncomfortable for the animal. Alternative embodiments can have connections which can be adjusted or changed to accommodate virtually any size animal.

Figure 7:
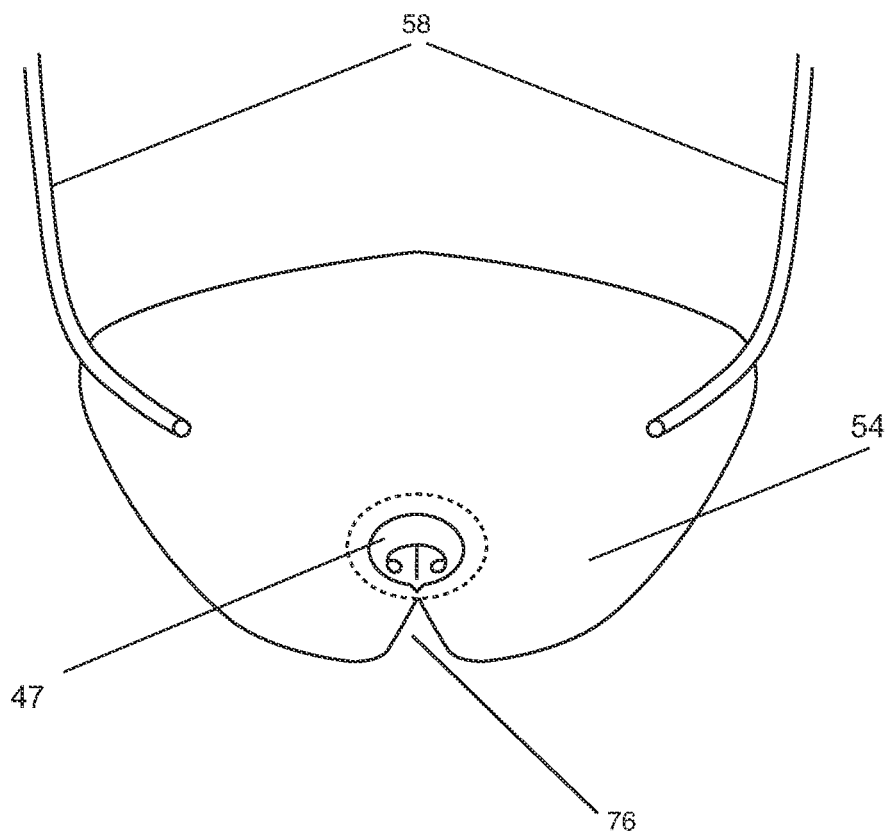
FIG. 7 illustrates placement of a mask of an embodiment of the present invention on an animal.

FIG. 7 illustrates a close up view of an embodiment of mask 54 with delivery tubes 58 that connect to the inside of mask 54. A nose of animal 47 is illustrated to demonstrate a preferred position and orientation of mask 54 on animal 47. In one embodiment of mask 54, notch 76 is preferably positioned at the center of the lower edge thereof to accommodate an upper lip of animal 47. Optionally, notch 76 in mask 54 provides an animal with more comfort for its lips and mouth.

FIGS. 8A and 8B illustrate embodiments of an underchin strap of the present invention. In this embodiment, chin strap 56 is disposed from the animal's chin upward and comprises fastened closure 57 around oxygen inlet tubes 58. Closure 57 can be on each side of the animal's face 47, to keep tubes and mask 54 close to a top of the animal's nose without making it uncomfortably tight over the nose. FIG. 8B illustrates underchin strap 56 with fasteners 75 e.g., hook and loop) that comprise a secure fit and removal prevention over inlet tubes 58 while permitting normal mouth movements. Other fasteners (e.g., snaps, buttons, pins, hooks, etc.), may also be used in accordance with the present invention.

Figure 9A:
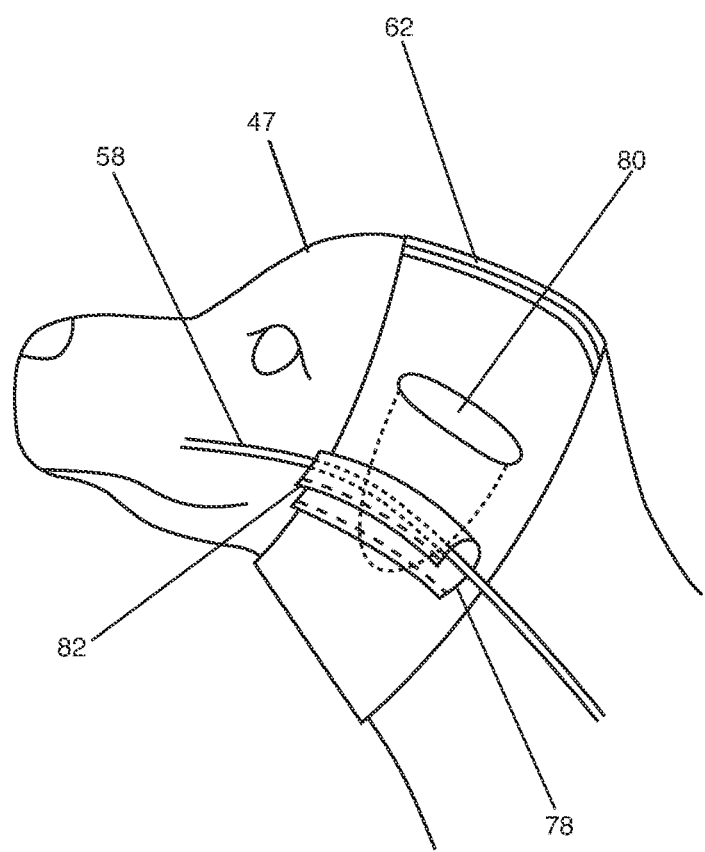

FIGS. 9A and B illustrate close up views of head strap 62. Head strap 62 preferably comprises fasteners 84 (e.g., hook and loop) disposed on top of the animal's head (FIG. 9B), and ear holes 80. Other fasteners (e.g., snaps, buttons, pins, hooks, etc.), may also be used in accordance with the present invention. Guide pockets 78 optionally secure supply tubes on an animal's head. In one embodiment, guide pockets 78 can be stitched onto head strap 62, facing away from an animal's face, to keep supply tubes disposed at the sides of the nose without letting them move up into an animal's vision. Optionally, opening 82 (FIG. 9A) of guide pocket 78 aids in providing a proper orientation of inlet tube 58, thereby positioning mask 54 (see FIG. 8A) for more direct blow-by.

Figure 9B:
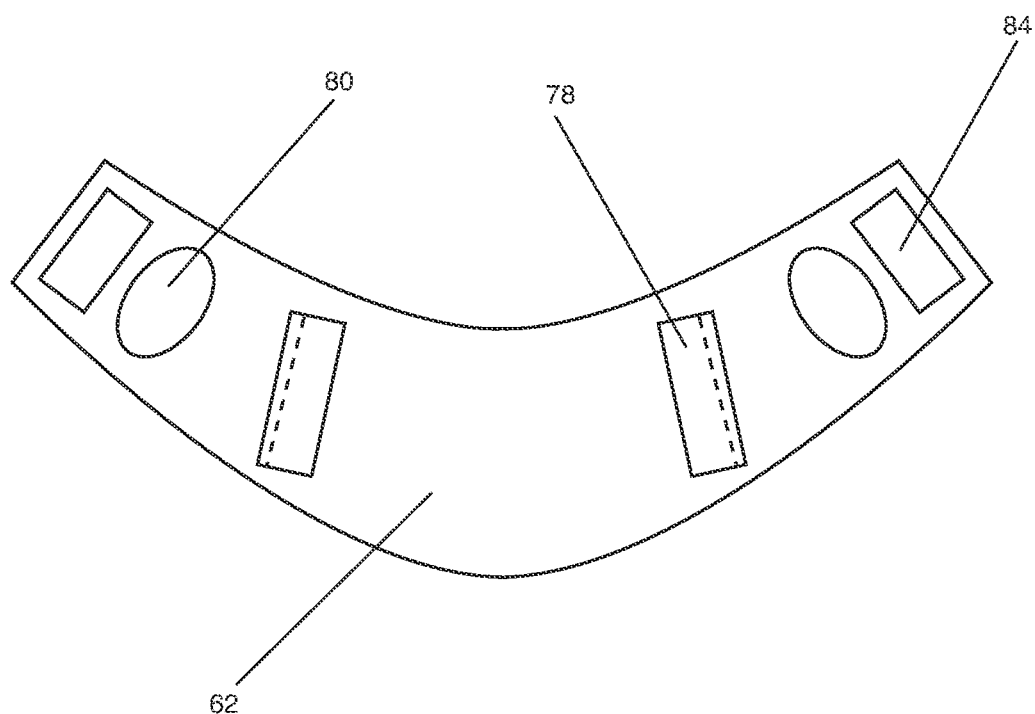
Figure 10:
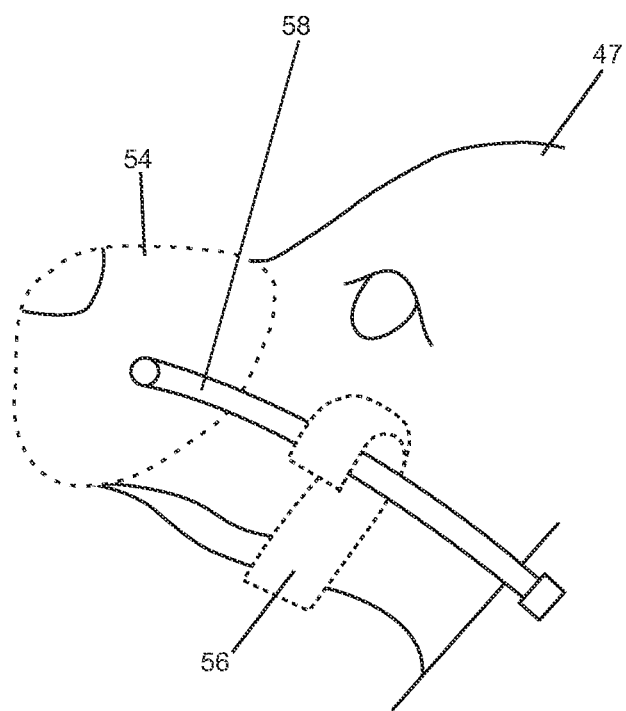
FIG. 10 illustrates a close up view of oxygen inlet tubes according to an embodiment of the present invention.
Figure 11:
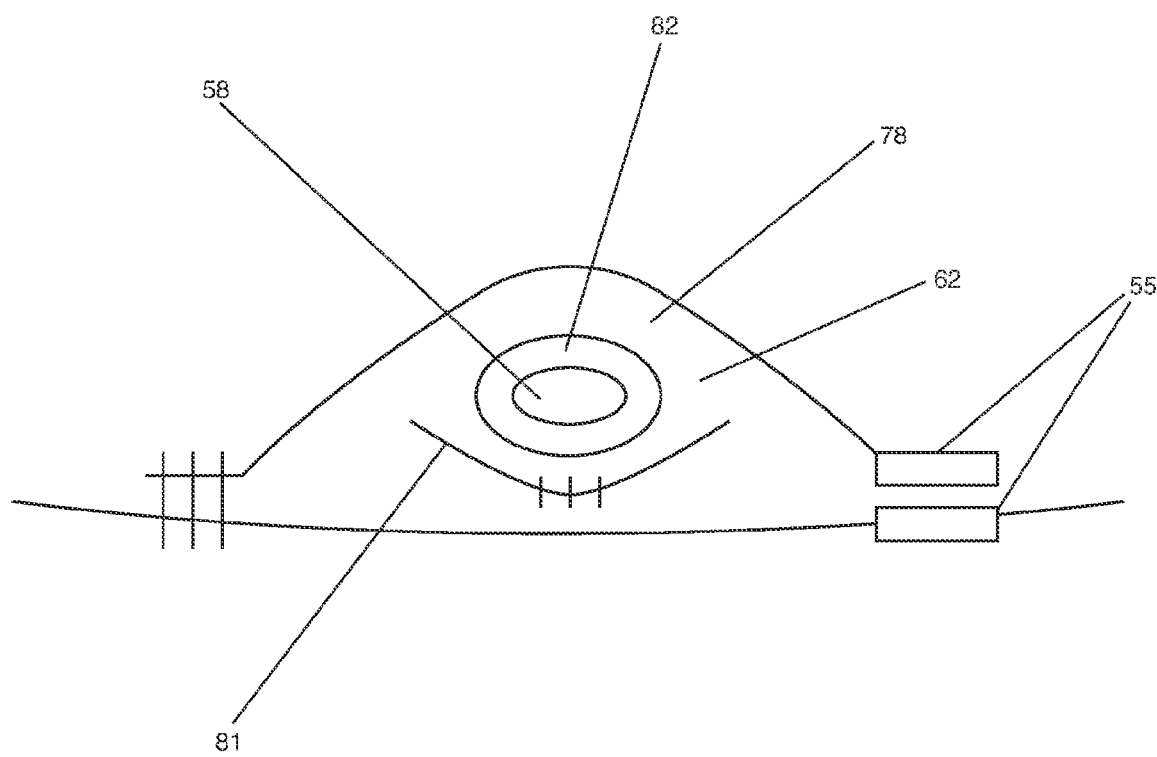
FIG. 11 illustrates a front view of an embodiment of a positioning pocket and an oxygen inlet tube.

Head strap 62 can have a plurality of functions (see FIGS. 9A and 9B). For example, head strap 62 can hold various components of the present invention in place without making animal 47 uncomfortable. In particular, it is desirable that the ears, eyes, and mouth not be covered or over stimulated, or distorted from their normal positions. Head strap 62 helps prevent crimping of inlet tubes 58, thus keeping them open. In addition, head strap 62 keeps inlet tubes 58 properly oriented toward mask 54. Embodiments of head strap 62 preferably comprise a lightweight, breathable, stretch fabric, and most preferably, one with a wide zigzag stitch, so as to permit stretching in multiple directions. Alternative embodiments include, but are not limited to, any fabric and/or any stitching and/or any combination thereof. Embodiments of guide pockets 78 on head strap 62 disposed on either cheek are preferably as nearly invisible to the animal as possible in its field of view. Therefore, embodiments of guide pockets 78 preferably comprise a stiff gutter to hold and direct inlet tubes 58. FIG. 10 illustrates an embodiment of inlet tube 58 positioned outside of the animal's field of view. FIG. 11 illustrates an embodiment (expanded view) of guide pocket 78 holding inlet tube 58, and opening 82 of guide pocket 78. FIG. 11 also illustrates an embodiment of guide pocket 78 comprising gutter 81 that optionally projects forward from the front edge of guide pocket 78 allowing underchin strap 62 to exert a downward hold while preventing crimping of inlet tubes 58. Fastener 55 can comprise one or more removable fasteners, permanent fasteners, semi-permanent fasteners and/or a combination thereof. Stitching 53 attaches guide pocket 78 to head strap 62.

An embodiment of the present invention provides various locations of ear holes 80 on head strap 62, that are pre-marked or partially pre-cut such that a user can cut and/or otherwise remove them as needed in order to accommodate a particular animal type and/or size. Alternatively, ear holes 80 are optionally not pre-cut in head strap 62 at its terminal end facing away from animal 47.

Guide channels 78 for inlet tubes 58 can be disposed on head strap 62 on opposite sides of a snout of animal 47 and symmetrically arranged relative to the animal's center line (under the chin, running down the front of the neck).

Figure 12:
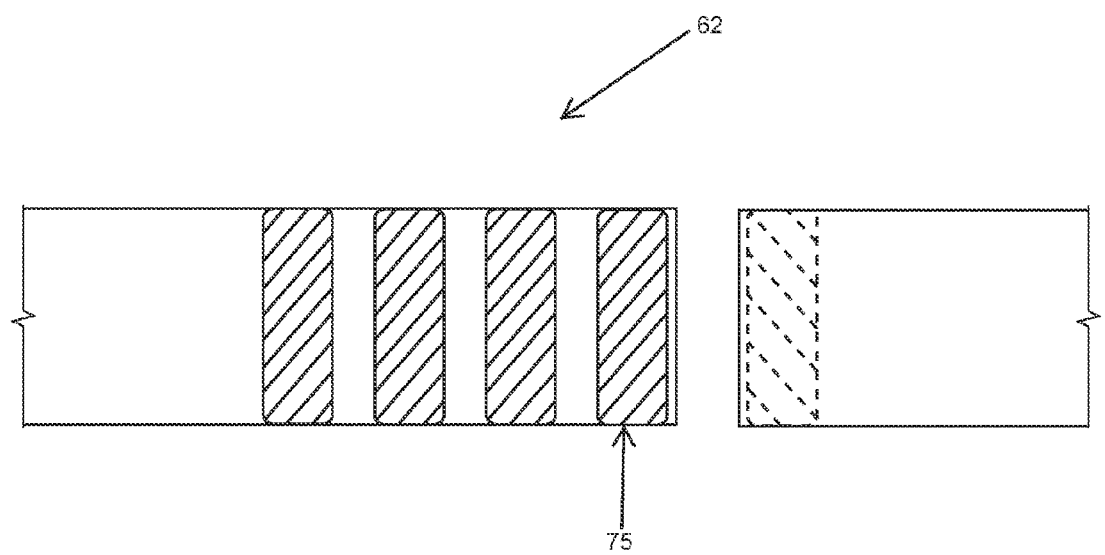
FIG. 12 illustrates a close up view of an embodiment of the head strap.

FIG. 12 is an illustration of a portion of head strap 62, and showing fasteners 75 (e.g., hook and loop). Other fasteners (e.g., snaps, buttons, pins, hooks, etc.), may also be used in accordance with the present invention. The total girth of head strap 62 can optionally be adjusted by having a series of fasteners 75 in parallel at the opposite terminal end.

Figure 13A:
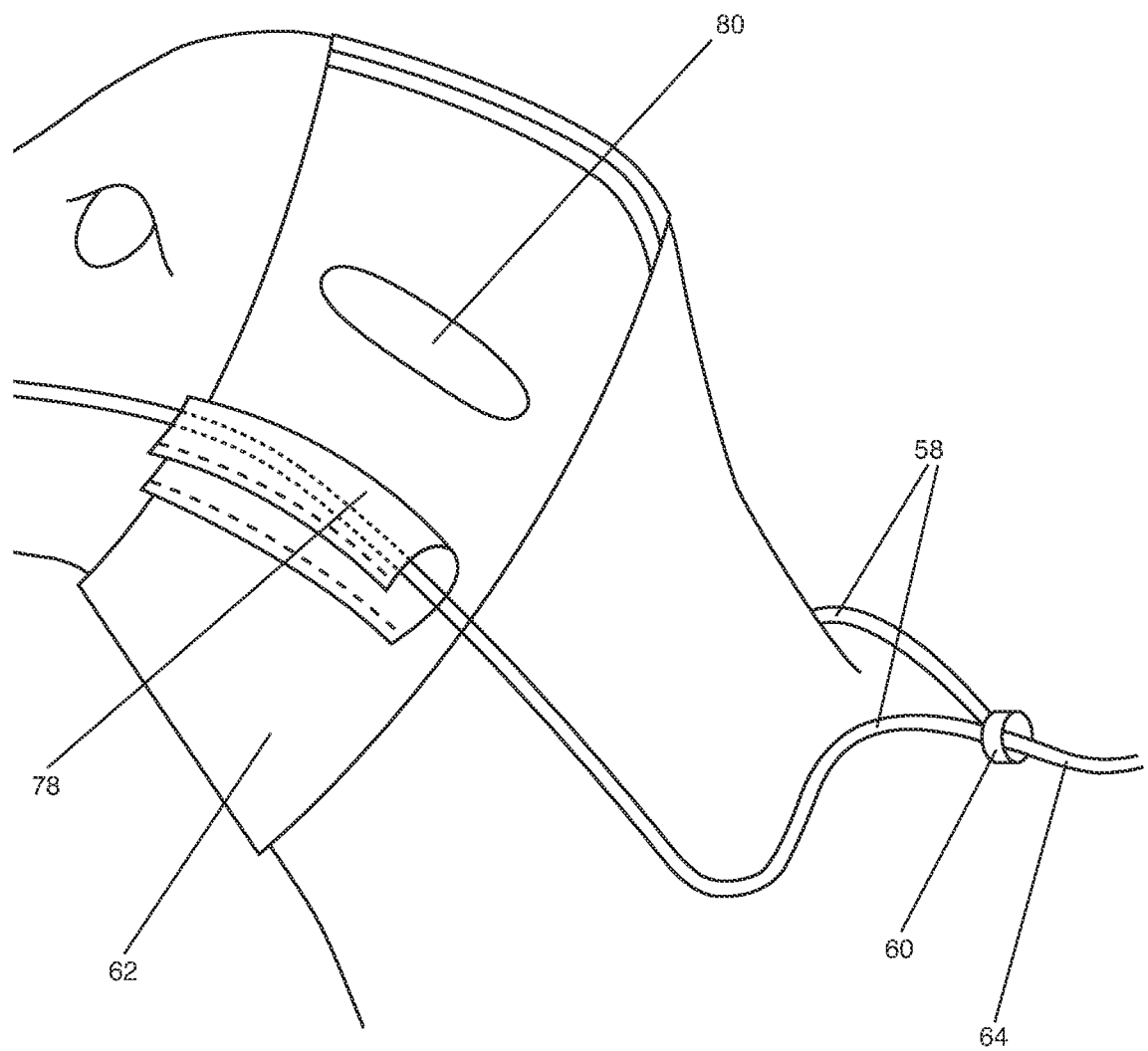
FIGS. 13A-C illustrate alternative embodiments of chocks according to embodiments of the present invention.
Figure 13B:
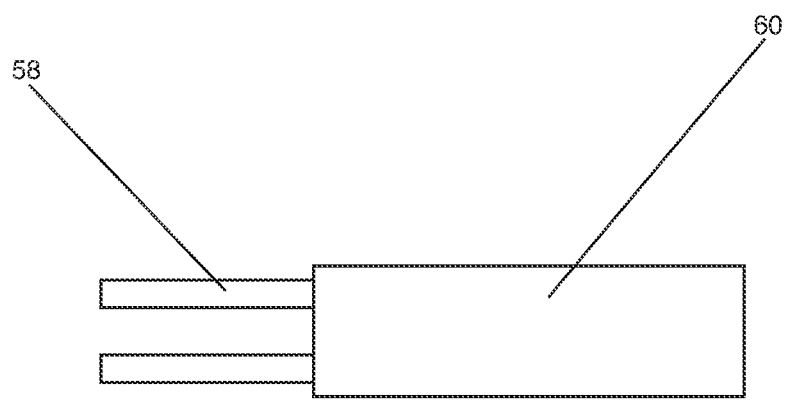
Figure 13C:
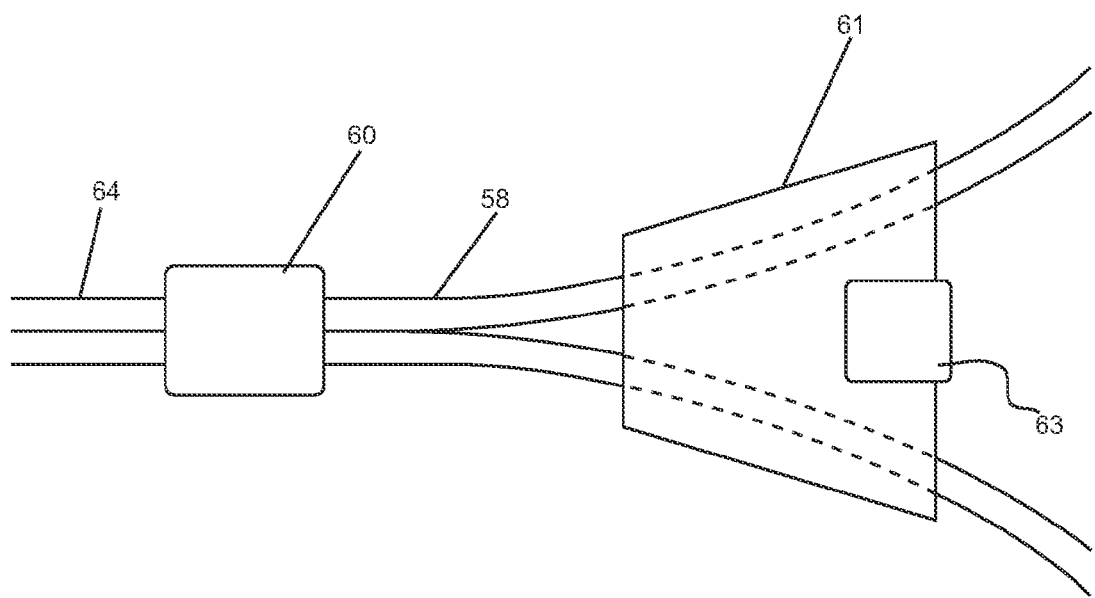

As illustrated in FIGS. 13A-13C, oxygen inlet tubes 58 preferably connect to transport tube 64 by friction fit chock 60. Friction fit chock 60 can be easily manufactured and easily adjusted, by sliding and/or pulling tight and/or repositioning, to remove some or all slack from the delivery tubes. Friction fit chock 60 preferably remain fixed in place after adjustment until tubes 58 stretch, at which time friction fit chock 60 can be easily opened, moved, and closed again.

Friction fit chock 60 is optionally fitted on the two delivery tubes (see also FIG. 13C), just after they exit the male fitting. It separates the two tubes so they are started at a natural angle on their paths around either side of the head.

Inlet tubes 58 preferably comprise soft and stretchy tubes. Chock 60 secures mask 54 tight against the nose of and prevents the animal from removing mask 54. Transport tube 64 is preferably attached so it projects off of an animal's back, out of the animal's main line of vision and attention, and can easily be attached and detached from supply tube 72. FIG. 13B illustrates an embodiment of friction fit chock 60. Chock 60 preferably comprises a rigid plastic, or similar material, and chock 60 preferably splits transport tube 64 into a plurality of inlet tubes 58 (see also FIG. 12).

FIG. 13C illustrates an alternative embodiment of a chock comprising triangular piece 61 with inner block 63. Block 63 can be pulled out of triangular piece 61, and inlet tubes 58 can slide easily through, in order to loosen tubes. Tubes 58 can be set in place and block 63 pushed back into triangular piece 61 and thereby tightened at the correct tension. Both pieces of triangular piece 61 can optionally have grooves and/or half tunnels to hold inlet tubes 58 firmly without squeezing them shut. As with other embodiments of tightening mechanisms, they can be placed on the tubes by sliding, and/or opening, adjusting, and locking into place. The easy adjustability of triangular piece 61 is preferable because inlet tubes 58 can stretch.

Figure 14A:
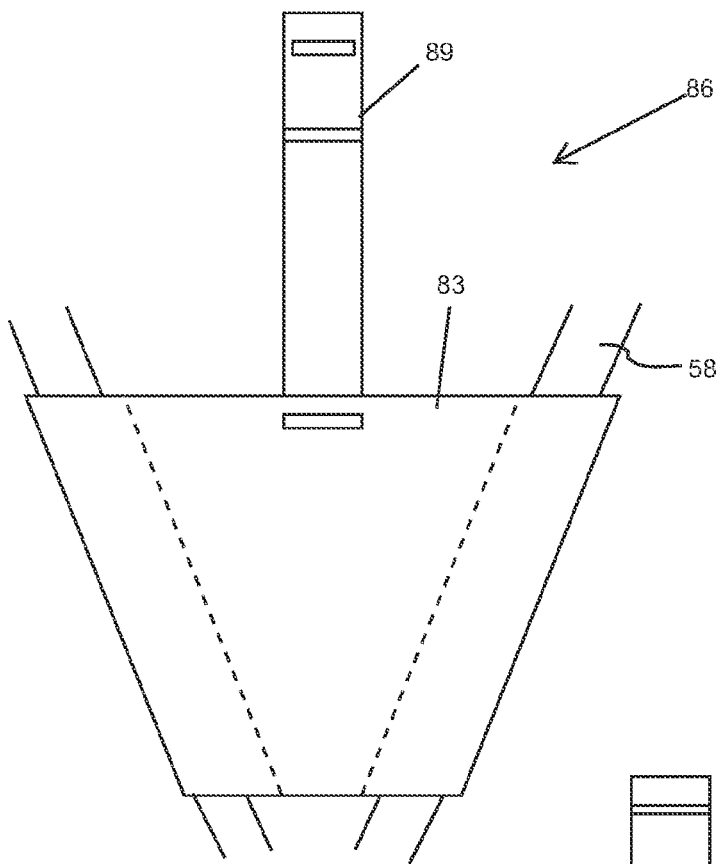
FIGS. 14 A-C illustrate exploded views of alternative embodiments of chocks.
Figure 14B:
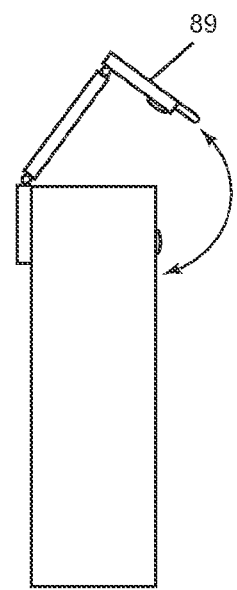
Figure 14C:
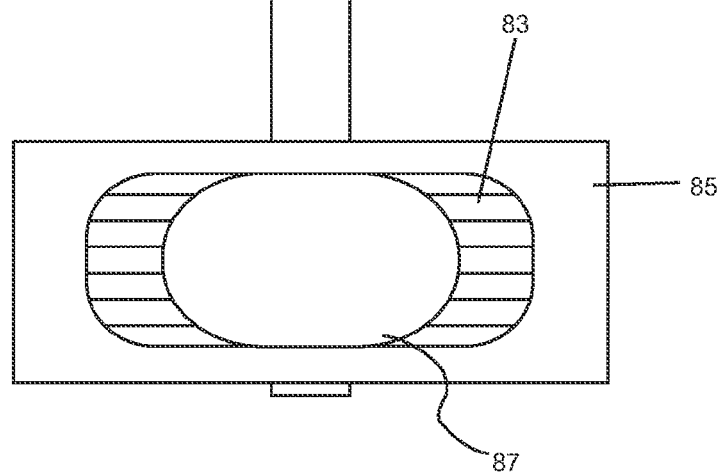

FIGS. 14 A-C and 15 A-D illustrate components of an alternative embodiment of chock 86 comprising a wedge-like shape to complete connection between inlet tube 58 and transport tube 64. This embodiment includes, but is not limited to, small, flat funnel 85 with two-channel fasteners. This embodiment is preferably in two parts, one part comprising funnel 85 (see FIG. 14 C) and the other flat wedge 83 (see FIG. 15B) with grooves 91 down its sides (see FIGS. 15C and 15D). This embodiment provides wedge 83 that is pushed inside the funnel 85, at opening 87 and squeezes inlet tubes 58 between wedge 83 and funnel 85 down the sides of grooves 91, holding them firmly in place without shutting off the flow of fluid and/or medication traveling through tubes 58. Retention strap 89 suffices to lock wedge 83 in place. Embodiments of fastener 89 are preferably inaccessible to the animal.

Figure 16:
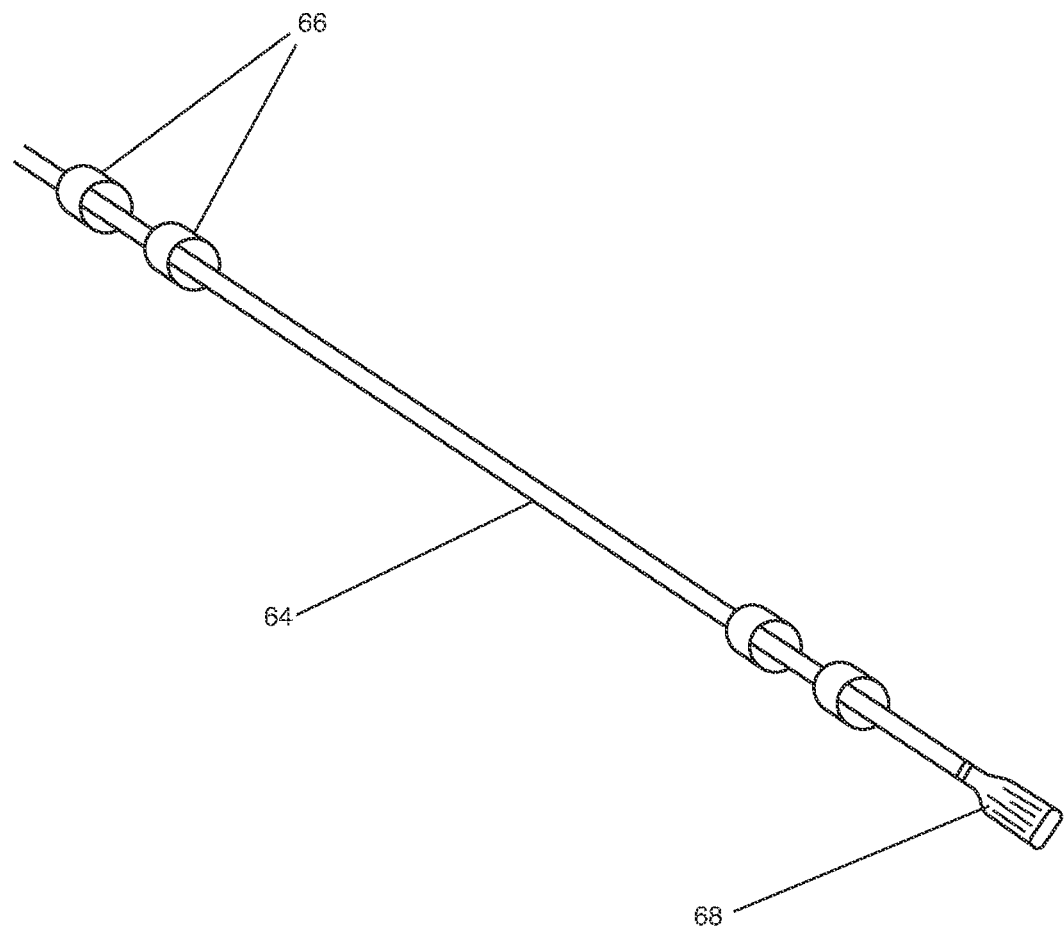
FIG. 16 illustrates an embodiment of an oxygen supply tube.

Referring now to FIG. 16, transport tube 64 is preferably loose enough along the animal's spine not to draw its attention constantly, and must be anchored tightly enough to prevent loosening. Tube 64 can have a range of looseness along its long axis, since the overall length of the animal's spine will change slightly according to his position and movement. The weight of tube 64 can be distributed over a wider area by disposing bumpers 66 around tube 64. Bumpers 66 are preferably disposed on top of belts 70 and thus transfer the weight of tube 64 onto belts 70, where it is thus transferred across the width of the animal (see also FIG. 18).

Figure 17:
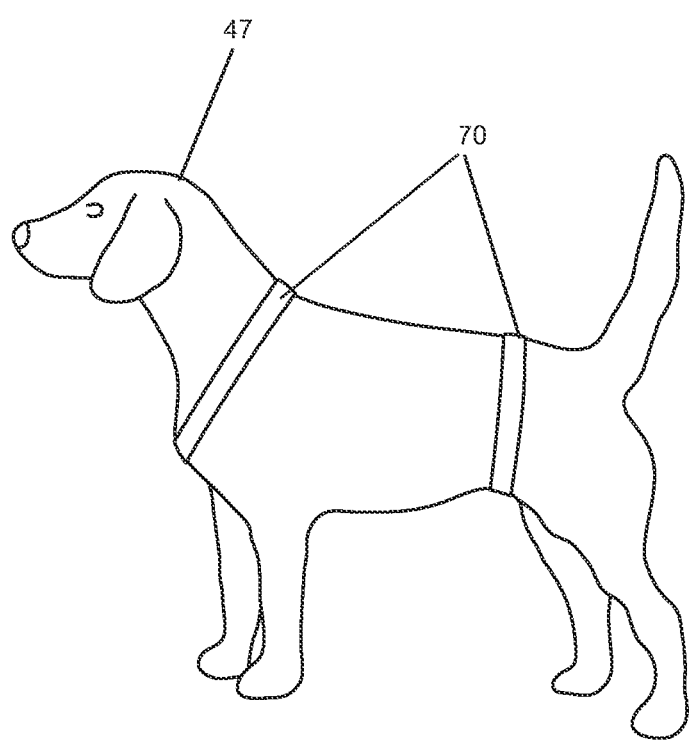
FIG. 17 illustrates stretch belts according to an embodiment of the present invention.

In an embodiment of the present invention as illustrated in FIG. 17, one of belts 70 can preferably be disposed around the chest of animal 47, similar to the front strap of a dog harness. Thus, it is preferably low on the animal's neck to keep it from twisting or traveling without being tight and constricting on animal 47. Another of belts 70 can be disposed around the animal's waist, for example in the case of a dog, it can be disposed around its torso directly in front of its hind legs, and can assist in holding transport tube 64 (see FIG. 18).

Belts 70 preferably have at least one fastener, closed tabs, or loops at the top, openable so a tube can be removed for cleaning or repositioning. Belts 70 can optionally be narrow to cover a minimum amount of space and be as unobtrusive as possible, while wide enough to spread the friction load.

Figure 18:
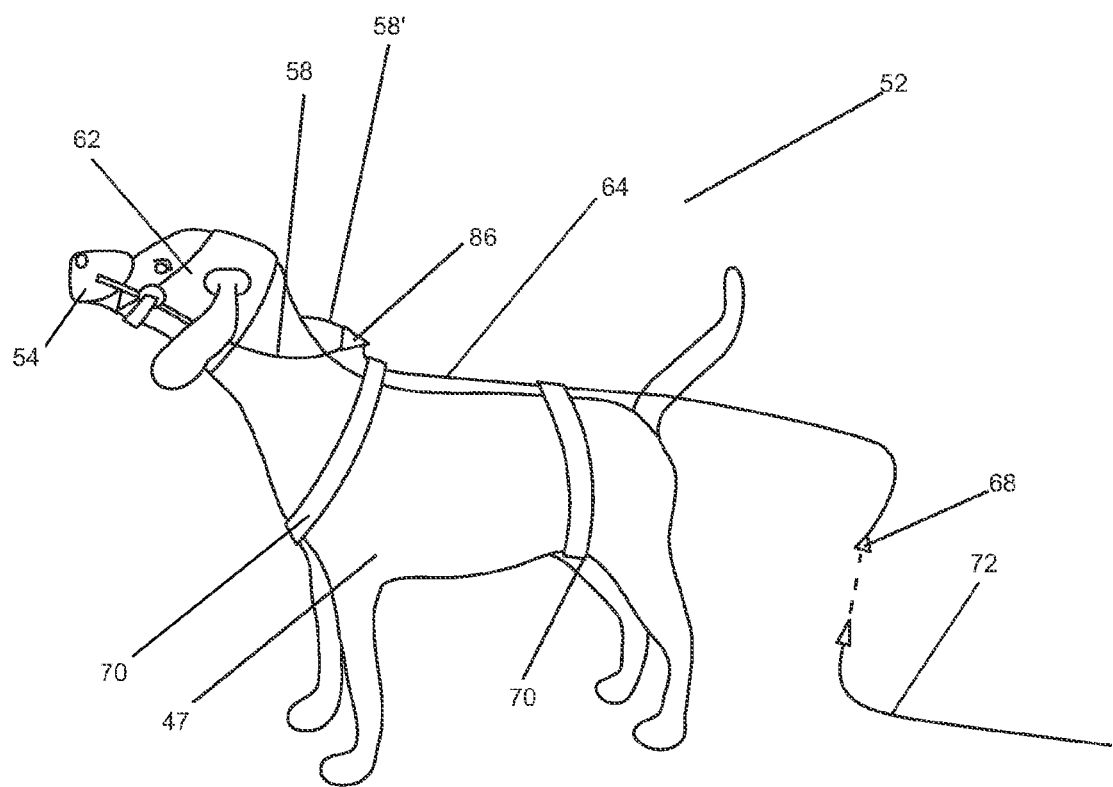
FIG. 18 illustrates an alternative embodiment of the present invention.

FIG. 18 illustrates an embodiment of the present invention. Animal oxygen delivery system 52 on animal 47 comprises mask 54, one or more inlet tubes 58, chock 86, head strap 62, belts 70, transport tube 68 and oxygen supply tube 72.

Dimensions of the components of the embodiments of the invention can be configured to accommodate measurements of the type and size of animal for which the invention is to be used. Alternative embodiments can also provide adjustment mechanisms on the various components such that a range of animals and/or sizes of an animal can be accommodated.

The present invention can be used at home by any animal owner, without special training, without intervention by a veterinarian and without risk of overdose.

Alternative embodiments of the present invention can comprise an elastomeric material, including but not limited to rubber and/or silicone washers that fit snugly around the transport tube to enable adjustment and tightening or loosening of various components of the present invention. Other embodiments optionally employ a self-tightening friction adjustment, for example by providing components that are formed at least partially from elastic materials.

An embodiment of the present invention is preferably used with non-human animals. An embodiment of the present invention is not useful for large animals, e.g., equine. An embodiment of the present invention is preferably used with four-legged animals having a weight of less than about 300 pounds, more preferably used with four-legged animals having a weight of less than about 100 pounds, and more preferably used with four-legged animals having a weight of less than about 50 pounds, and most preferably used with four-legged animals having a weight of less than about 25 pounds. In one embodiment, the present invention is self-supportive and does not require a user to hold the mask of the present invention in place. An embodiment of the present invention is preferably positionable on a cat and/or dog. An embodiment of the present invention can be attached to an animal and the animal allowed to move about in at least a given area without requiring a human to hold or move a component of the present invention.

INDUSTRIAL APPLICABILITY

The present invention is further illustrated by the following non-limiting examples.

EXAMPLE 1

The present invention was reduced to practice and experimentally tested on the inventor's 14-15 pound dog (named Dr. Robert). Dr. Robert had a mysterious illness which was finally diagnosed as Interstitial Lung Disease. Interstitial Lung Disease is the gradual occlusion of empty space in the lung with scar tissue and fluid, choking off the ability to expand the lung and draw in air. He was very near death, even in an oxygen cage at a veterinary facility. The veterinarian was unable to raise his blood oxygen concentration above 88% until he inserted and sewed in place an oxygen catheter, which brought it up to 94%, a level that can sustain life. He was still restrained in intensive care and was very uncomfortable, foaming from the nose around the catheter and trying repeatedly to claw it out. Dr. Robert could not be held or taken outside because of this. He was restricted to 15 seconds at a time off of the hose. Euthanasia was clearly the treatment of choice.

The inventor, not willing to accept euthanasia for Dr. Robert, and wanting to bring him home, developed the present invention. Using a combination of sewing, glue, heat, and friction fastening, a prototype of an embodiment of the present invention was created. The inventor then went back to the veterinarian, had them remove the catheter, and installed an embodiment of the present invention on Dr. Robert. His blood oxygen concentration went up to 98%, dropped back to 96%, and stayed there. Dr. Robert was able to go home.

Dr. Robert was a Cavalier King Charles Spaniel, a breed that has very long, soft, furry ears. The head strap was designed to keep his ears comfortable, but out of his water and food bowls. The stiff channels for the supply tubes were made from some polyethylene lab tubing, which were cut lengthwise, flattened temporarily, and sewed with a line of straight stitching along the midline. Straight stitching was used because the tubing was non-stretch. The tube projected about ⅝ inches beyond the front of the head strap, leaving room for the chin strap to be fastened around both a gutter and supply line. If the gutter ended where the head strap did, the chin strap could pull the supply tube down and crimp it. All parts of the head strap were closed with a fastener so they could be opened for removal, repositioning, and cleaning of the oxygen tubes. All fasteners had to be placed so that the stiff, prickly male side, with hooks, faced away from the dog's skin, and only the soft, loop female side faced the skin. The chin strap also needed similar closures at both ends so it could be placed under the chin, wrapped around the two guide gutters, and adjusted to be just tight enough to hold the supply tubes down in the proper position so the mask could not easily be rubbed up and off the nose.

As Dr. Robert's symptoms were identified, the flow was increased or decreased as necessary. With "blow-by" oxygen, there is no possibility of an overdose. This meant that no special training, without intervention by a veterinarian, was necessary to deliver oxygen to Dr. Robert.

The present invention can be used at home by any animal owner, without special training, without intervention by a veterinarian and without risk of overdose.

In the weeks that followed, the design was refined to make it more securely attached, yet more comfortable, for Dr. Robert. Within a few days, his breathing had improved enough to unplug his hose and let him go out the dog door in the usual way to attend to his bathroom needs. When he came back in, he was always somewhat oxygen starved, but reconnecting him to a supply of oxygen rapidly improved his gum color and balance. He resumed his normal life, seeming less and less sick, and was able to sleep in a bed, play with his toys and his fellow dogs, eat normally, and go out in the garden with his fifty-foot transport hose.

Options that have been incorporated to address adjustability include but are not limited to marking the transport tube with calibrating marks, and supplying the tube (the rear end of the transport tube as yet uncut and unconnected) with a separate fitting that will have a male insert to go into the transport tube, back-to-back with a female receptacle for the "industrial" connector. The transport tube was placed along the animal's back, marked where to cut the tube, and how to cut it. The tube was double checked to ensure there were no small remnants of adhesive after the connector was glued to the tube inside the tube that could block oxygen flow. Once the measurement was made, the tube was cut, and the connector glued to it, it was set for long-term use.

The following were the dimensions of the various components:

Front belt dimensions were: overall length, including overlap for Velcro® hook and loop tape closure: 21 inches; approximate overlap for closure: 2 inches.

For retention of transport tube on top of belt: overall length 2.5 inches, of which 0.5 inches between stitching at attached end and beginning of Velcro® hook and loop tape, to provide a smooth tight fit around transport tube; 1.5 inches female Velcro® hook and loop tape; 0.5 inches ribbon sewn over non-attached end for ease of grasping and opening Velcro® hook and loop tape to make adjustments. Belt: overall length, including overlap for Velcro® hook and loop tape closure: 18 inches.

End supply tubes: 11 inches from center of mask to junction where two supply tubes originate from transport tube; this distance variably shortened to keep tubes and mask snug against his face, but not so tight as to be uncomfortable.

Chinstrap: overall length, unstretched, 17 inches, with about 1.5 inches of this devoted to Velcro® hook and loop tape closure.

Head strap was made of Lycra® fabric, very stretchy, so when installed and stretched out so as to give close but not tight fit, the real head-and-neck circumference was probably about 18 inches.

Transport tube: from point of emergence of supply tubes from junction to tip of male connector at end: 14.75 inches.

For five weeks of mostly continuous oxygen therapy, combined with oral and inhaled steroids, his breathing had improved so much that the veterinarian recommended taking him off it for slowly increasing periods. He was able to breathe unaided for three days at a time over the course of many weeks.

Note that in the specification and claims, "about" or "approximately" means within twenty percent (20%) of the numerical amount cited.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. An apparatus for providing fluid to a dog, the apparatus comprising:
    a fluid delivery system comprising at least one mask and at least one fluid transport tube for delivery of a fluid source to said mask;
    a head strap;
    said head strap comprising one or more tube guide pockets adapted to be disposed behind eyes of the dog and below ears of the dog when said apparatus is disposed on the dog in its intended operating position;
    said apparatus adapted to maintain said fluid transport tube outside of a field of view of the dog when said apparatus is disposed on the dog in its intended operating position;
    said tube guide pockets positioned such that a primary axis of said fluid transport tube pass therethrough and are at least substantially perpendicular with a long axis of said head strap;
    at least one chock adapted to provide a tight fit of said fluid transport tube against the dog when said apparatus is disposed on the dog; and
    at least one securing belt for disposing said fluid delivery system on the dog.

2. The apparatus of claim 1 wherein said fluid delivery system comprises a flexible mask.

3. The apparatus of claim 1 wherein said securing belt comprises at least one underchin strap.

4. The apparatus of claim 1 wherein said securing belt comprises a harness.

5. The apparatus of claim 1 wherein said fluid delivery system is adapted to hold said fluid transport tube out of reach of teeth of the dog.

6. The apparatus of claim 1 wherein said fluid delivery system is adapted to not require a human to hold said delivery system on the dog after the delivery system is disposed on the dog.

7. The apparatus of claim 1 wherein said apparatus is configured to allow the dog to eat, drink, sneeze, scratch, sleep in many positions, walk, run, and twirl while the dog is wearing said apparatus.

8. The apparatus of claim 1 wherein the fluid comprises oxygen.

9. The apparatus of claim 1 wherein the fluid comprises a medication.

10. A method for providing a fluid to a dog, the method comprising:
    providing a fluid delivery system comprising a mask for delivery of a fluid to the dog;
    securing the fluid delivery system to the dog with at least one securing belt;
    disposing the mask at least partially around a nose of the dog;
    causing a fluid to travel through the fluid delivery system, from a fluid source, through at least one tube and into the mask;
    passing the dog's ears through ear holes disposed in a head strap, the head strap comprising one or more pockets for the fluid delivery system, wherein the pockets are adapted to be positioned behind an eye of the dog when the delivery system is disposed on the dog in its intended operating position;
    maintaining the at least one tube outside of a field of view of the dog when the fluid delivery system is disposed on the dog in its intended operating position;
    adjusting the at least one tube tight against the dog with a chock; and
    the method performed without requiring a person to hold the delivery system on the dog after the fluid delivery system is attached to the dog.

11. The method of claim 10 further comprising securing the at least one tube to the dog with a strap.

12. The method of claim 11 further comprising securing the at least one tube to the dog with said head strap.

13. The method of claim 11 further comprising securing the at least one tube to the dog with an underchin strap.

14. The method of claim 10 further comprising securing the at least one tube to the dog with a harness.

15. The method of claim 10 further comprising supporting at least a portion of the tube with the fluid delivery system such that the tube is out of reach of the dog's teeth.

16. The method of claim 10 wherein providing at least one fluid source comprises providing an oxygen source and wherein the fluid comprises oxygen.

17. The method of claim 10 wherein providing the fluid to the dog allows the dog to eat, drink, sneeze, scratch, sleep in many positions, walk, run, twirl, and engage in normal behavior.

18. The method of claim 10 wherein the fluid comprises a medication.

* * * * *